(12) United States Patent
Meyer

(10) Patent No.: US 7,077,824 B2
(45) Date of Patent: Jul. 18, 2006

(54) SINGLE USE SAFETY SYRINGE

(75) Inventor: Gysbert Albertus Meyer, Pretoria (ZA)

(73) Assignee: African Ventures and Technology (Pty) Ltd., Pretoria (ZA)

( * ) Notice: Subject to any disclaimer, the term of this patent is extended or adjusted under 35 U.S.C. 154(b) by 226 days.

(21) Appl. No.: 10/489,501

(22) PCT Filed: Sep. 13, 2002

(86) PCT No.: PCT/ZA02/00142

§ 371 (c)(1),
(2), (4) Date: May 25, 2004

(87) PCT Pub. No.: WO03/022335

PCT Pub. Date: Mar. 20, 2003

(65) Prior Publication Data

US 2004/0243066 A1 Dec. 2, 2004

(30) Foreign Application Priority Data

Sep. 13, 2001 (ZA) .................... 01/7538
Oct. 1, 2001 (ZA) .................... 01/8031

(51) Int. Cl.
 *A61M 5/00* (2006.01)
 *A61M 5/315* (2006.01)
 *A61M 5/32* (2006.01)
(52) U.S. Cl. .................. 604/110; 604/228; 604/192
(58) Field of Classification Search ............... 604/110, 604/192, 198, 263, 164.08, 218, 220, 228
See application file for complete search history.

(56) References Cited

U.S. PATENT DOCUMENTS

| | | | | |
|---|---|---|---|---|
| 1,921,034 A | * | 8/1933 | La Marche | 604/157 |
| 4,573,976 A | | 3/1986 | Sampson et al. | |
| 4,699,614 A | * | 10/1987 | Glazier | 604/110 |
| 4,775,363 A | * | 10/1988 | Sandsdalen | 604/110 |
| 4,795,443 A | * | 1/1989 | Permenter et al. | 604/198 |
| 4,883,466 A | | 11/1989 | Glazier | |
| 4,915,696 A | * | 4/1990 | Feimer | 604/192 |
| 4,994,046 A | * | 2/1991 | Wesson et al. | 604/198 |
| 5,026,356 A | * | 6/1991 | Smith | 604/192 |
| 5,312,372 A | | 5/1994 | DeHarde et al. | |
| 5,411,492 A | * | 5/1995 | Sturman et al. | 604/263 |
| 5,466,223 A | * | 11/1995 | Bressler et al. | 604/110 |
| 5,672,161 A | | 9/1997 | Allen et al. | |
| 5,702,369 A | | 12/1997 | Mercereau | |
| 6,013,056 A | * | 1/2000 | Pettersen | 604/110 |
| 6,213,987 B1 | | 4/2001 | Hirsch et al. | |

FOREIGN PATENT DOCUMENTS

| | | |
|---|---|---|
| EP | 0 308 380 | 3/1989 |
| EP | 0 709 105 | 5/1996 |
| FR | 2 635 686 | 3/1990 |
| FR | 2 676 928 | 12/1992 |
| GB | 2 282 069 | 3/1995 |
| WO | 89/04185 | 5/1989 |
| WO | 90/02575 | 3/1990 |

* cited by examiner

*Primary Examiner*—Sharon Kennedy
(74) *Attorney, Agent, or Firm*—Merchant & Gould P.C.

(57) ABSTRACT

A safety device for a syringe needle, which includes a guide and a slidable member having a first portion that is configured to be slid along the guide and a second portion having a formation for a needle, that facilitates the shielding of the sharp point within said formation. A non-reusable syringe, which includes a plunger having a first part with one or more followers and a second part housing a guide.

9 Claims, 9 Drawing Sheets

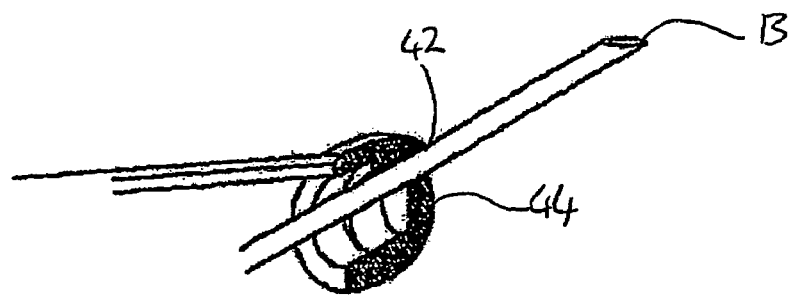
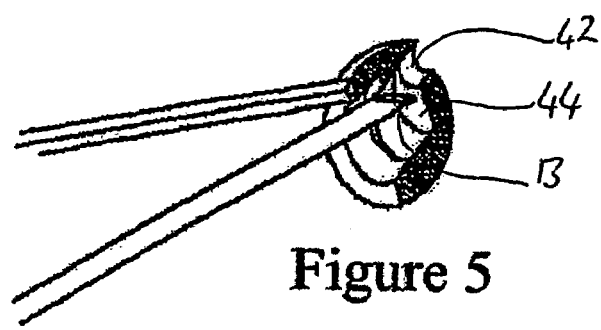
Figure 5
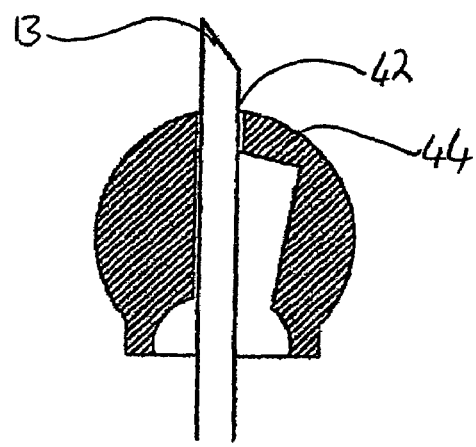
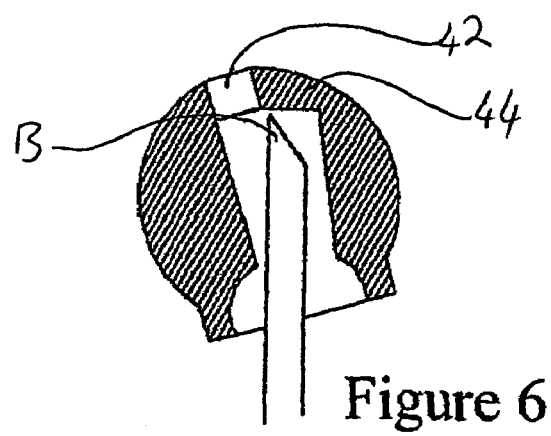
Figure 6

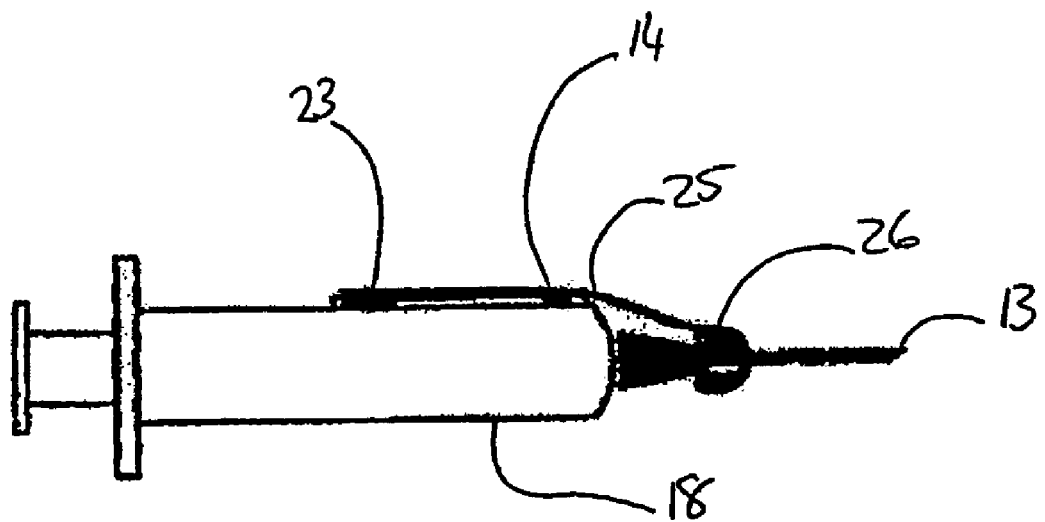
Figure 7[a]
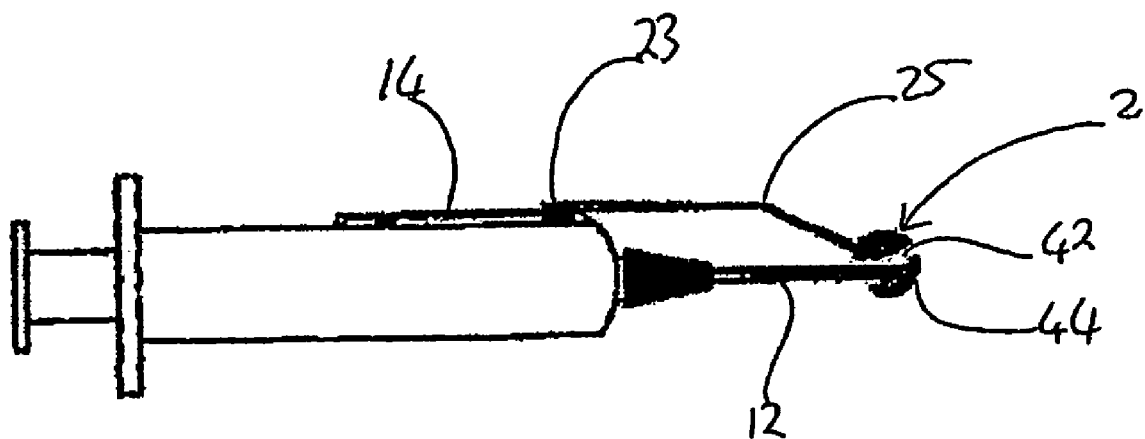
Figure 7[b]

SINGLE USE SAFETY SYRINGE

FIELD OF THE INVENTION

The present invention lies in the field of safety syringes, particularly those that prevent needle stick injuries and that are rendered permanently non-reusable.

BACKGROUND

With the ever-increasing risk of acquiring the Human Immunodeficiency Virus and other blood-born infections, a need exists for a reliable, easy-to-use and cost effective safety syringe that minimizes the exposure of the healthcare worker and patient. A multitude of proposals have been made in the field. However these generally exhibit disadvantages such as requiring both hands of the healthcare worker to operate and/or having a high manufacturing cost. The cost of medical care in impoverished third world countries has resulted in the re-use of disposable medical equipment, often without adequate sterilization. In light of the high incidence of HIV and related illnesses in these countries, this situation is unacceptable. Patient education is often not optimal, and the unsophisticated patient is more likely to accept re-used equipment. Available mechanisms to render syringes non-reusable have been found to be expensive and some are even made re-usable by the determined user.

THE INVENTION

The present invention provides a safety device for a syringe needle which includes, a guide mounted on the barrel of a syringe or being an integral moulded part of the barrel, a slidable member with a first portion configured to be slid along the guide and a second portion having a formation for a needle, that facilitates the shielding of the sharp point within that formation.

The guide has proximal and distal ends. The proximal end is defined by a terminal block that prevents the first portion of the slidable member from disengaging from the guide at the proximal end, a bevelled segment that allows for connection with the first portion of the slidable member and a chamfered segment to facilitate the temporary positioning of the first portion before the slidable member is advanced to engage with the needlepoint. The distal end of the guide is defined by a segment of aligned toothed serrations that, when in use, engage with a complementary segment on the first portion of the slidable member and thereby lock the slidable member in a non-retractable position with the needle enclosed within the second portion.

The first portion of the slidable member consists of a bracket and a shaft. The bracket is configured to snap-click onto the bevelled segment of the guide The second portion of the slidable member may be in the form of a cup- or cap shaped formation for a needle or an eccentric aperture for said needle with a closed segment for shielding the needle.

The first portion of the slidable member can be resiliently deformable and biased e.g. away from the barrel of the syringe, so that when the slidable member is advanced towards the needle, until the cap slips off the end of the needle, since the aperture or formation provided for the needle is angled away from the needlepoint, the point is thereby shielded within the cap.

The inventor believes that the safety syringe only needs one hand for rendering the needlepoint safe and thereby allows the healthcare worker to utilise the other hand for patient care and to keep the other hand away from the needlepoint.

Another aspect of the invention is a means of making a syringe non-reusable and consists of a plunger having a first part with one or more followers a second part housing a guide for receiving and guiding the followers.

A sealing plug may be attached to the end of the plunger or may form a single unit with the second part of the plunger. The second part of the plunger may in itself comprise two portions—a first portion housing the guide, and a second portion that serves as a means for connecting the sealing plug.

The guide can consist of at least two legs with an apex, but can also be Z- or M-shaped.

A M-shaped guided guide can include a first, second, third and fourth leg, with a first apex point between the first and second leg, a second apex point between the second and third leg and a third apex point between the third and fourth leg.

At the first, second and third apex point a means is provided for to ensure a one-directional pathway of the followers in the guide. This means may be in the form of compressible moulded protrusions with a stepped incline preventing re-entry into a preceding leg. The first leg of the M-shaped guide receives the follower, as the plunger is advanced in the syringe. The first leg can be used to prepare the syringe to the position needed to draw fluid into the syringe, or it can be used to inject an amount of air into another vial. It is preferable that the follower is assembled within the guide and that the plunger is inserted into the barrel opening before the syringe is used. Once the follower has advanced along the first leg, the first apex of the M-shaped guide is configured to encourage a path towards the second leg of the M-shaped guide.

The second leg of the M-shaped guide, guides the follower as the plunger is pulled away from the needle end of the syringe. This action will correspond with the filling of the syringe of medication, body fluids and the like.

The second apex is configured to encourage a path towards the third leg of the M-shaped guide. The third leg of the M-shaped guide receives the follower as the plunger is pushed towards the needle end of the syringe. This action corresponds with the administering of the content to the patient or the depositing of the blood or fluid sample in an appropriate container. The third apex point then encourages a path towards the fourth leg of the M-shaped guide, if an attempt is made to re-use the syringe or to remove the plunger from the barrel of the syringe. The fourth leg of the M-shaped guide receives the follower as the plunger is drawn back from the needle end of the syringe. This fourth leg is in communication with the exterior of the second part of the plunger and thereby allows the follower to slide out of the M-shape guide and thereby disassociates the first part of the plunger from the second part and thus causes the second part and the plunger to remain at the needle end of the syringe. The needle can be pre-manufactured with the syringe and non-removable.

A Z-shaped guide can include a first, second and third leg, with a first apex point between the first and second leg and a second apex point between the second and third leg. In this instance the syringe would typically be ready for use with the plunger fully inserted into the barrel of the syringe. The first and second apex can have a means for encouraging a one-directional pathway of the followers. This means can be in the form of compressible moulded protrusions with a stepped incline preventing re-entry into a preceding leg.

The first leg of the Z-shape, receives the follower as the plunger is pulled away from the needle end of the syringe. The first apex is configured to encourage a path towards the second leg of the Z-shape. The second leg of the Z-shape receives the follower as the plunger is pushed towards the needle end of the syringe. On reaching the second apex point, a path towards the third leg of the Z-shape is encouraged. The third leg of the Z-shape receives the follower as the plunger is drawn back from the needle end of the syringe, and this third leg of the Z-shape is then in communication with the exterior of the plunger and in so doing allows the follower to slide out of the Z-shape guide and thereby disassociates the first part of the plunger from the second part of the plunger, causing the second part to remain at the needle end of the syringe. The needle can be pre-manufactured with the syringe and non-removable.

A V-shaped guide and can include a first and second leg, with an apex point between the first and second leg. A means for encouraging a one-directional pathway of the followers can be located within the apex and can be in the form of compressible moulded protrusions with a stepped incline preventing re-entry into a preceding leg.

The first leg of the V-shape, receives the follower as the plunger is pushed towards the needle end of the syringe. Upon reaching the apex, the follower can be encouraged to follow a path towards the second leg of the V-shape.

The second leg of the v-shape receives the follower as the plunger is pulled away from the needle end of the syringe.

This second leg of the V-shape is in communication with the exterior of the plunger and in so doing allows the follower to slide out of the V-shape guide and thereby disassociates the first part of the plunger from the second part of the plunger, causing the second part to remain at the needle end of the syringe.

The non-reusable syringe with a V-shaped guide can be a pre-filled syringe and/or the needle can be a pre-manufactured part of the syringe.

THE DRAWINGS

The invention is more fully described by way of a non-limiting example, with reference to the drawings, in which:

FIGS. 5 and 6 are enlarged views of the formation for the needle

FIGS. 7[a] and [b] show the safety syringe in use.

Figure 1:
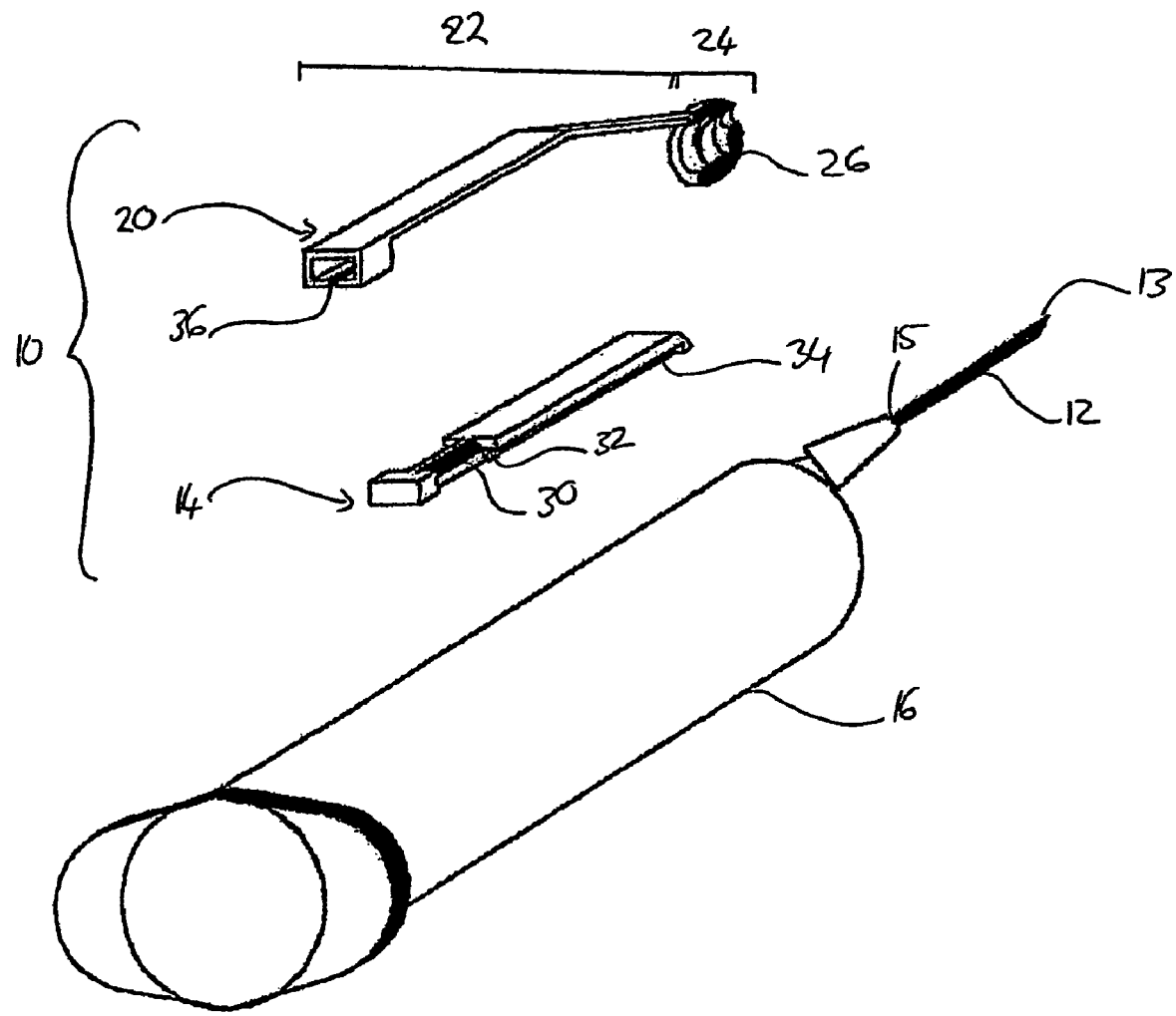
FIG. 1 is a drawing of the safety device and a syringe.
Figure 2:
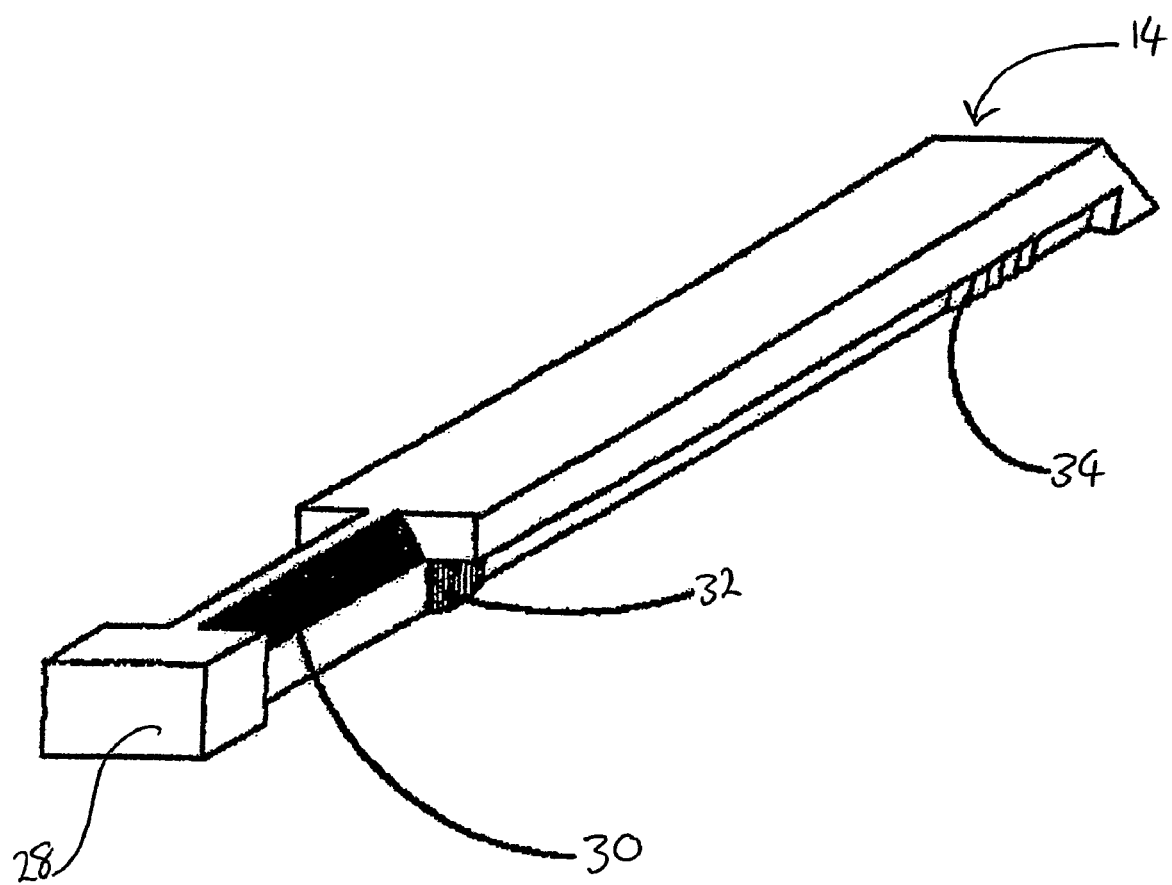
FIG. 2 is an enlarged view of the guide.
Figure 3:
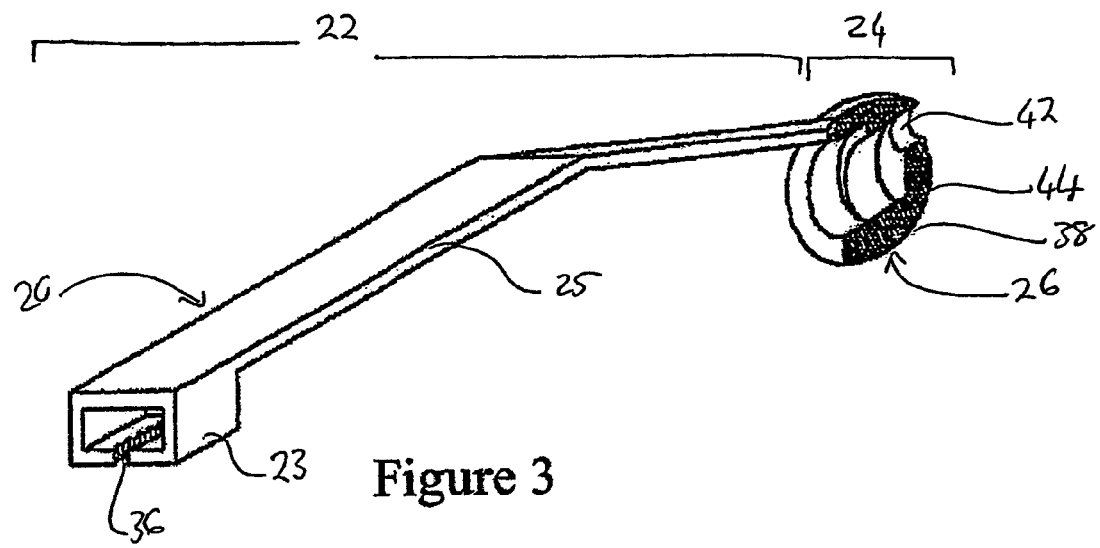
FIG. 3 and FIG. 4 are enlarged views of the slidable member of the safety device.
Figure 4:
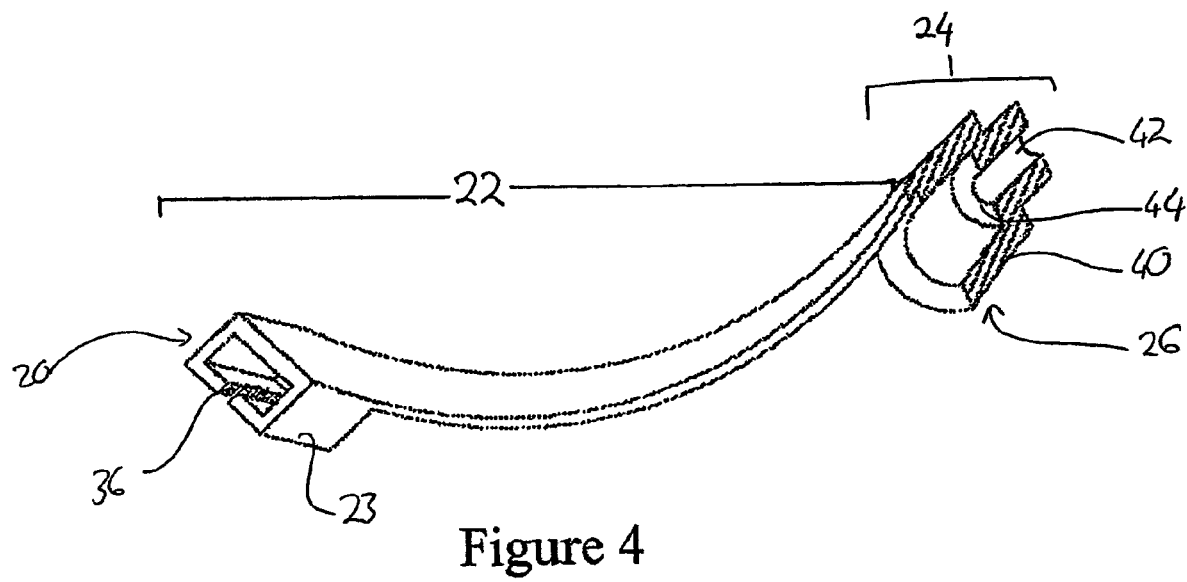
Figure 8:
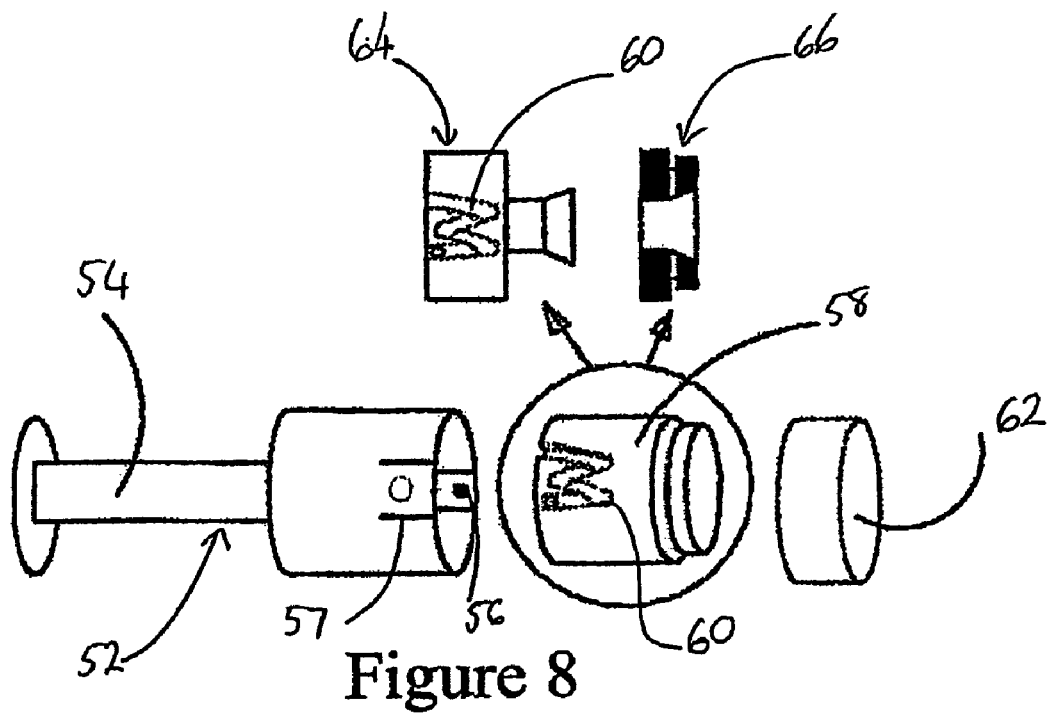

FIG. 8 is a drawing of the plunger for a non-reusable syringe.

Figure 9:
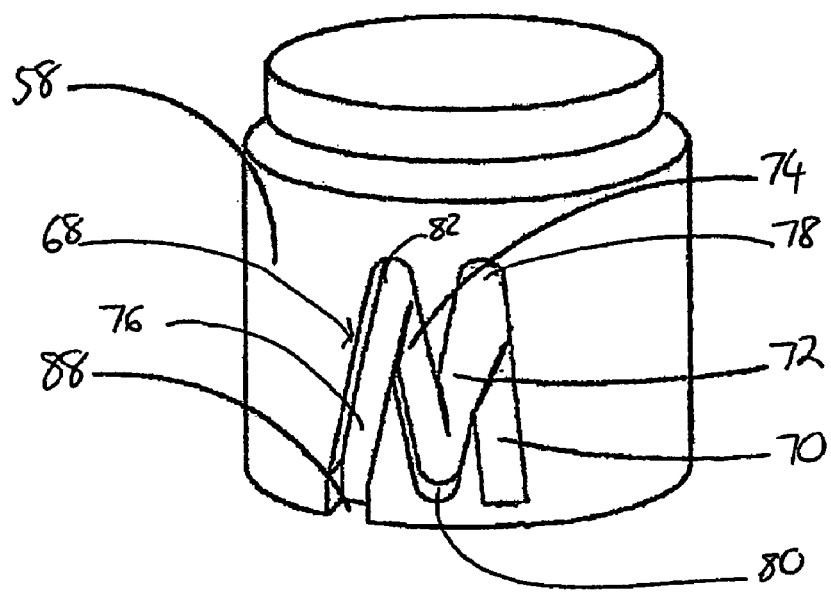

FIG. 9 is an enlarged view of the guide.

Figure 10:
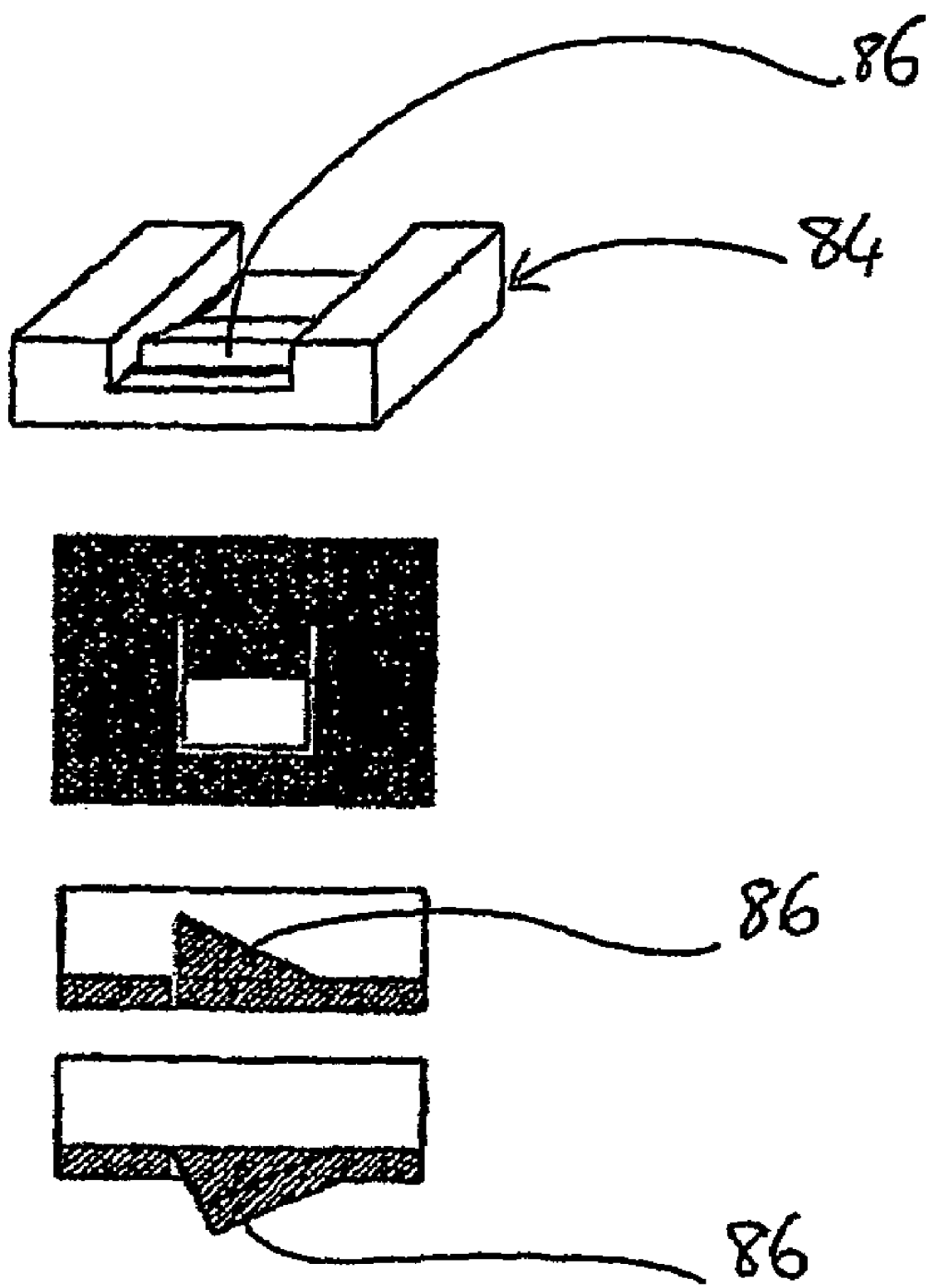

FIG. 10 is a drawing of the protrusions within the apex points.

Figure 11:
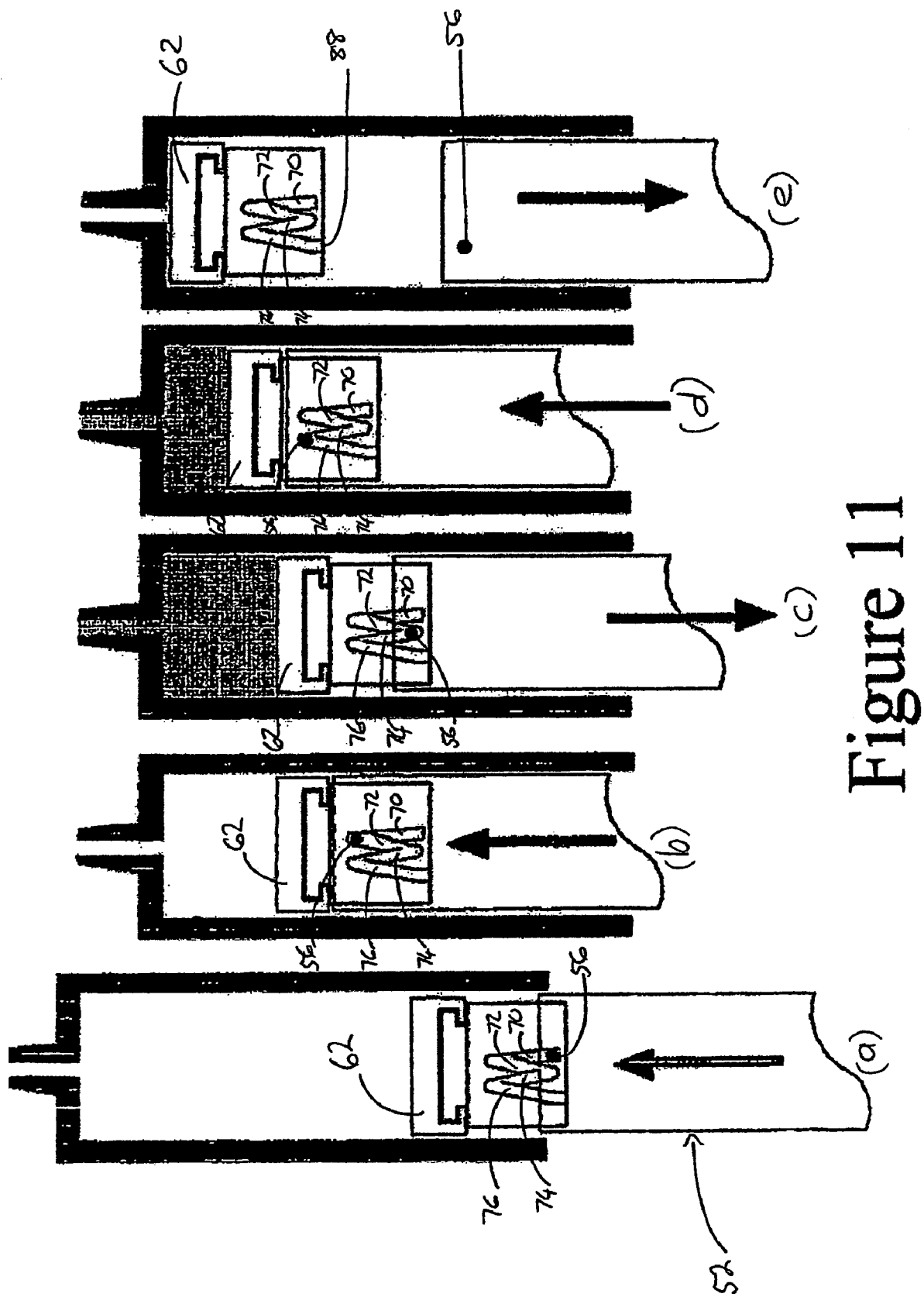

FIGS. 11 [a] to [e] show the syringe in use

Figure 12:
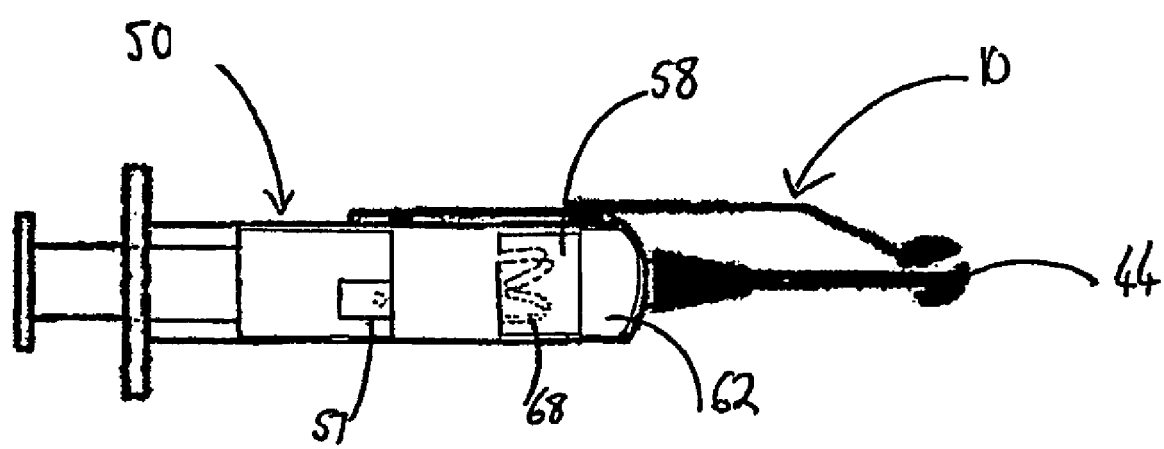

FIG. 12 shows a combined non-reusable safety stringe.

THE PREFERRED EMBODIMENTS

As shown in the FIGS. 1 to 7, the safety device 10 for a syringe needle 12 includes, a guide 14 mounted on the barrel 16 of a syringe 18 or being an integral moulded part of the barrel 16 and a slidable member 20 with a first portion 22 configured to be slid along the guide 14 and a second portion 24 having a formation 26 for a needle 12, that facilitates the shielding of the sharp point 13 within that formation 26.

The guide 14 has proximal and distal ends. The proximal end is defined by a terminal block 28 that prevents the first portion 22 of the slidable member from disengaging from the guide 14 at the proximal end, a bevelled segment 30 that allows for connection with the first portion 22 of the slidable member and a chamfered segment 32 to facilitate the temporary positioning of the first portion 22 before the slidable member 20 is advanced to engage with the needlepoint 13. The distal end of the guide 14 is defined by a segment of aligned toothed serrations 34 that, when in use, engage with a complementary segment 36 on the first portion 22 of the slidable member 20 and thereby lock the slidable member 20 in a non-retractable position with the needlepoint 13 shielded by the formation for the needle 26.

The first portion 22 of the slidable member 20 consists of a bracket 23 and a shaft 25. The bracket 23 is configured to snap-click onto the bevelled segment 30 of the guide 14.

The second portion 24 of the slidable member 20 has a formation 26 for a needlepoint 13 in the form of a cup shape 38 or a cap 40. The formation 26 has an eccentric aperture 42 for said needlepoint 13 with a closed segment 44 for shielding the needlepoint 13. The needle 12 penetrates the aperture 42 of the formation 26, thereby causing the formation 26 to rest at the base of the needle 15 when the bracket 23 of the slidable member 20 is positioned on the chamfered segment 32. The first portion 22 of the slidable member 20 can be resiliently deformable and biased away from the barrel 16 of the syringe 18 so that when the slidable member 20 is advanced towards the needle 12, until the cap 40 slips off the end of the needlepoint 13, since the aperture 42 or formation 26 provided for the needle 12 is angled away from the needlepoint 13, the point is thereby shielded by the cap 40 6r c4–44 [see FIGS. 7[a] and [b].

The slidable member of the safety syringe enables only one hand to be used for rendering the needlepoint safe and thereby allows the healthcare worker to utilise the other hand for patient care and to keep the other hand away from the needlepoint.

According to another aspect of the invention, as shown in FIGS. 8 to 11, a non-reusable syringe 50 that has a plunger 52, having a first part 54 with one or more followers 56, in the form of nipples on flexible flaps 57 and a second part 58 housing a guide 60 for receiving and guiding the followers 56.

A sealing plug 62 may be attached to the end of the plunger 52 or may form a single unit with the second part 58 of the plunger 52. The second part 58 of the plunger 52 may in itself comprise two portions- a first portion 64 housing the guide 60, and a second portion 66 that serves as a means for connecting the sealing plug 62.

The guide 60 can consist of at least two legs with an apex (viz. V-shaped), but can also be Z- or M-shaped.

A M-shaped guide 68 can include a first 70, second 72, third 74 and fourth 76 leg, with a first apex point 78 between the first 70 and second 72 leg, a second apex point 80 between the second 72 and third 74 leg and a third apex point 82 between the third 74 and fourth 76 leg.

At the first 78, second 80 and third 82 apex point a means 84 is provided for to ensure a one-directional pathway of the followers in the guide. This means may be in the form of compressible moulded protrusions 86 with a stepped incline preventing re-entry into a preceding leg. The first leg 70 of the M-shape receives the follower 56, as the plunger 52 is advanced in the syringe 50. The first leg 70 can be used to prepare the syringe 50 to the position needed to draw fluid into the syringe 50, or it can be used to inject an amount of air into another vial. It is preferable that the follower 56 is assembled within the guide 60 and that the plunger 52 is inserted into the barrel opening 53 before the syringe 50 is used. Once the follower 56 has advanced along the first leg 70, the first apex 78 of the M-shaped guide 68 is configured to encourage a path towards the second leg 72 of the M-shaped guide 68.

The second leg 72 of the M-shaped guide 68, guides the follower 56 as the plunger 52 is pulled away from the needle end 51 of the syringe 50. This action will correspond with the filling of the syringe of medication, body fluids and the like.

The second apex 80 is configured to encourage a path towards the third leg 74 of the M-shaped guide 68. The third leg 74 of the M-shaped guide 68 receives the follower 56 as the plunger 52 is pushed towards the needle end 51 of the syringe 50. This action corresponds with the administering of the content to the patient or the depositing of the blood or fluid sample in an appropriate container. The third apex point 82 then encourages a path towards the fourth leg 76 of the M-shaped guide 68, if an attempt is made to re-use the syringe 50 or to remove the plunger 52 from the barrel of the syringe 50. The fourth leg 76 of the M-shaped guide 68 receives the follower 56 as the plunger 52 is drawn back from the needle end 51 of the syringe 50. This fourth leg 76 is in communication with the exterior 88 of the second part 58 of the plunger 52 and thereby allows the follower 56 to slide out of the M-shaped guide 68 and thereby disassociates the first part 54 of the plunger 52 from the second part 58 and thus causes the second part 58 and the plunger 52 to remain at the needle end 51 of the syringe 50.

The needle can be a pre-manufactured part of the syringe.

REFERENCE NUMERALS

10—Safety device
12—Needle
13—Needlepoint
14—Guide
15—Base of the needle
16—Barrel
18—Syringe
20—Slidable member
22—First portion of the slidable member
23—Bracket
24—Second portion of the slidable member
25—Shaft
26—Formation
28—Terminal block
30—Bevelled segment
32—Chamfered segment
34—Serrations on guide
36—Serrations on slidable member
38—Cup-shaped formation
40—Cap-shaped formation
42—Eccentric aperture
44—Closed segment
50—Non-reusable syringe
51—Needle end of the syringe
52—Plunger
53—Barrel opening
54—First part of the plunger
56—Followers
57—Flexible flaps with nipples
58—Second part of the plunger
60—Guide
62—Sealing plug
64—First portion of second part
66—Second portion of second part
68—M-shaped guide
70—First leg
72—Second leg
74—Third Leg
76—Fourth leg
78—First apex
80—Second apex
82—Third apex
84—One directional flow means
86—Protrusions
88—Communication point

The invention claimed is:

1. A safety device for a syringe which has a barrel and a needle, which safety device includes
    a guide;
    a slidable member having a first portion that is configured to be slid along the guide and positioned relative to the guide in a pre-determined position, the first portion including a bracket and a resiliently deformable shaft biased away from the barrel; and
    a second portion of the slidable member attached to the shaft, wherein the second portion has a shielding formation, a part of the shielding formation facilitating shielding of a point of the needle when the shaft is biased away from the barrel of the syringe.

2. A safety device as claimed in claim 1, wherein the shielding formation is in the form of a cap that facilitates the shielding of the needle-point.

3. A safety device as claimed in claim 1, wherein the second portion of the slidable member consists of an eccentric aperture and a closed segment, the closed segment being adjacent the needle-point when the slidable member is advanced along the guide and the shaft is biased away the barrel of the syringe.

4. A safety device as claimed in claim 3, wherein the resiliently deformable shaft of the first portion causes the aperture of the formation to be biased away from the needle-point when the slidable member has been advanced along the guide and in so doing the closed segment has come to rest over the needle-point.

5. A safety device as claimed in claim 1, wherein the guide has a first end region which is configured to restrict further displacement of the slidable member relative to the guide and has a longitudinally opposite second end region, which is configured to engage the bracket of the slidable member, thereby discouraging displacement of the second portion from the needle-point.

6. A safety device as claimed in claim 5, wherein the bracket of the slidable member has an inner lip complementarily serrated to lock with toothed serrations on the second end region of the guide.

7. A non-reusable syringe, which includes;
    a plunger having a first part with at least one follower;
    a second part housing an M-shaped guide, whereby the follower on said first part is guided in a predetermined pathway, said guide including;
    a first, second, third and fourth leg, with a first apex position between the first and second leg, a second apex position between the second and third leg and a third apex position between the third and fourth leg, the guide including a means of encouraging a one-directional pathway of the followers, the means located at the positions of the first, second and third apexes and wherein the first leg of the M-shaped guide receives the follower, as the plunger is advanced in the syringe so as to expel substance within the syringe, the first apex of the M-shaped guide is configured to encourage a path towards the second leg of the M-shaped guide, the second leg of the M-shaped guide, receives the follower as the plunger is pulled away from the needle end of the syringe when the syringe is filled with a liquid, the second apex is configured to encourage a path towards the third leg of the M-shaped guide, the third leg of the M-shaped guide receives the follower as the plunger is pushed towards the needle end of the syringe to expel the liquid, the third apex position encourages a path towards the fourth leg of the M-shaped guide, the fourth leg of the M-shaped guide receives the follower as the plunger is drawn back from the needle end of the syringe and wherein the fourth leg of the M-shaped guide is in communication with the exterior of the plunger and in so doing allows the follower to slide out of the M-shaped guide and thereby disassociates the first part of the plunger from the second part of the plunger, causing the second part to be left behind at the needle end of the syringe.

8. A syringe as claimed in claim 7, wherein the second part of the plunger comprises two members, the first housing the guide and the second adapted to connect to a sealing plug attached to an end of the plunger.

9. A syringe as claimed in claim 7, wherein the means of encouraging the one directional pathway is in the form of compressible moulded protrusions with a stepped incline preventing re-entry into a preceding leg.

* * * * *